(12) United States Patent
Feith et al.

(10) Patent No.: US 11,998,723 B2
(45) Date of Patent: Jun. 4, 2024

(54) VENTED SYRINGE

(71) Applicant: Becton, Dickinson and Company, San Diego, CA (US)

(72) Inventors: Raymond Feith, San Diego, CA (US); Christopher Zollinger, San Diego, CA (US); George Mansour, Diamond Bar, CA (US); Edmond Yu, Chino Hills, CA (US); Tomas Frausto, San Diego, CA (US); Ryan Callahan, Long Beach, CA (US)

(73) Assignee: Becton, Dickinson & Company, San Diego, CA (US)

( * ) Notice: Subject to any disclaimer, the term of this patent is extended or adjusted under 35 U.S.C. 154(b) by 354 days.

(21) Appl. No.: 16/286,382

(22) Filed: Feb. 26, 2019

(65) Prior Publication Data

US 2020/0268976 A1    Aug. 27, 2020

(51) Int. Cl.
*A61M 5/31* (2006.01)
*A61J 1/20* (2006.01)
(Continued)

(52) U.S. Cl.
CPC .......... *A61M 5/3148* (2013.01); *A61J 1/2096* (2013.01); *A61M 5/1782* (2013.01);
(Continued)

(58) Field of Classification Search
CPC ........ A61M 2005/3123; A61M 5/3148; A61M 5/1782; A61J 1/2068; A61J 1/2037; A61J 1/2062
See application file for complete search history.

(56) References Cited

U.S. PATENT DOCUMENTS 1,643,531 A * 9/1927 Wolf ................. A61M 5/31511
604/125
2,861,571 A * 11/1958 Sandhage ............ A61M 5/204
604/184
(Continued)

FOREIGN PATENT DOCUMENTS

CN    102985122 A    3/2013
CN    205041911 U    2/2016
(Continued)

OTHER PUBLICATIONS

International Search Report and Written Opinion for Application No. PCT/US2020/019950, dated May 25, 2020, 16 pages.
(Continued)

*Primary Examiner* — Lauren P Farrar
(74) *Attorney, Agent, or Firm* — Morgan, Lewis & Bockius LLP

(57) ABSTRACT

Vented syringes are described herein. A vented syringe includes a syringe body and a plunger body. The syringe body defines a syringe cavity. The plunger body is at least partially disposed within the syringe cavity. The plunger body includes an air intake channel defined within the plunger body. The vented syringe further includes a plunger seal that is sealingly engaged with the syringe cavity to cooperatively define a syringe volume. The vented syringe further includes a one-way valve in fluid communication with the air intake channel and the syringe volume, wherein the one-way valve is configured to prevent fluid flow from the syringe volume to the air intake channel and permit fluid flow from the air intake channel to the syringe volume.

20 Claims, 6 Drawing Sheets

(51) Int. Cl.
*A61M 5/178* (2006.01)
*A61M 5/32* (2006.01)

(52) U.S. Cl.
CPC .......... *A61M 5/3221* (2013.01); *A61J 1/2068* (2015.05); *A61M 2005/3123* (2013.01)

(56) References Cited

U.S. PATENT DOCUMENTS

| | | | |
|---|---|---|---|
| 4,572,210 A | 2/1986 | McKinnon | |
| 4,660,569 A | 4/1987 | Etherington | |
| 4,952,210 A * | 8/1990 | Alchas | A61M 5/14 604/257 |
| 5,067,948 A * | 11/1991 | Haber | A61M 5/1782 604/220 |
| 5,181,909 A * | 1/1993 | McFarlane | A61M 5/315 604/191 |
| 6,716,187 B1 | 4/2004 | Jorgensen et al. | |
| 8,992,482 B2 * | 3/2015 | Fojtik | A61M 5/204 604/187 |
| 8,992,505 B2 * | 3/2015 | Thorne, Jr. | A61M 5/31596 604/184 |
| 9,713,679 B2 * | 7/2017 | Kay | A61M 5/385 |
| 2012/0197232 A1 * | 8/2012 | Lee | A61M 5/19 604/506 |
| 2012/0232524 A1 * | 9/2012 | Hyun | A61M 5/385 604/514 |
| 2017/0246087 A1 | 8/2017 | Davis | |

FOREIGN PATENT DOCUMENTS

| | | | |
|---|---|---|---|
| CN | 109310409 A | 2/2019 | |
| JP | S50081096 U | 7/1975 | |
| JP | 3114128 U | 9/2005 | |
| JP | 2014212805 A | 11/2014 | |
| JP | 2017221440 A | 12/2017 | |
| WO | WO-0100261 A1 * | 1/2001 | ........ A61M 5/31596 |
| WO | WO-2012139695 | 10/2012 | |

OTHER PUBLICATIONS

Chinese Office Action for Application No. 202080030091.7, dated Mar. 1, 2023, 22 pages including translation.
Chinese Office Action for Application No. 202080030091.7, dated Aug. 19, 2023, 24 pages including translation.
Chinese Office Action for Application No. 202080030091.7, dated Jan. 4, 2024, 31 pages including translation.
Japanese Office Action for Application No. 2021-549921, dated Dec. 26, 2023, 7 pages including translation.
European Office Action for Application No. 20713481.8, dated Mar. 15, 2024, 5 pages.

* cited by examiner

VENTED SYRINGE

FIELD OF THE INVENTION

The present disclosure generally relates to syringes, and, in particular, to vented syringes.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, an IV bag. Certain medical fluids may be transported in vials or other vessels other than an IV bag. Medical fluids transported in vials or other vessels may be retrieved and introduced to the IV set via intermediate syringes.

In some applications, during the use of medical fluids that are transported in vials or other vessels other than an IV bag, simplified medical procedures are desired.

SUMMARY

The disclosed subject matter relates to vented syringes. In certain embodiments, a vented syringe is disclosed that comprises a syringe body defining a syringe cavity; a plunger body disposed at least partially within the syringe cavity, the plunger body comprising an air intake channel defined within the plunger body and extending between a first end and a second end of the plunger body; a plunger seal disposed at the second end of the plunger body and sealingly engaged with the syringe cavity to cooperatively define a syringe volume within the syringe cavity; and a one-way valve in fluid communication with the air intake channel and the syringe volume, wherein the one-way valve is configured to prevent fluid flow from the syringe volume to the air intake channel and permit fluid flow from the air intake channel to the syringe volume.

In certain embodiments, a vented syringe is disclosed that comprises a syringe body defining a syringe cavity; a plunger body disposed at least partially within the syringe cavity, the plunger body comprising an air intake channel defined within the plunger body and extending between a first end and a second end of the plunger body; a plunger seal disposed at the second end of the plunger body and sealingly engaged with the syringe cavity to cooperatively define a syringe volume within the syringe cavity, wherein expansion of the syringe volume provides a vacuum within the syringe volume; and a one-way valve in fluid communication with the air intake channel and the syringe volume, wherein the one-way valve is configured to prevent fluid flow into the air intake channel during expansion of the syringe volume and permit fluid flow from the air intake channel to the syringe volume to release the vacuum within the syringe volume.

In certain embodiments, a method for introducing a medical fluid is disclosed that comprises expanding a syringe volume to introduce the medical fluid via an aperture in fluid communication with the syringe volume; and sealing an air intake channel from the syringe volume during the expansion of the syringe volume.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The disclosed vented syringe incorporates an air intake channel with a one-way valve. The air intake channel can be disposed within the plunger body to permit IV delivery of a medical fluid directly from the vented syringe. By delivering medical fluids directly from the vented syringe, IV sets can be simplified and reduced, and costs can be reduced. Further, the vented syringe can be utilized for plunger delivery of medical fluids, if desired.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to the administration of medical fluid to a patient by a medical practitioner using the disclosed vented syringe, it is to be understood that this description is only an example of usage and does not limit the scope of the claims. Various aspects of the disclosed vented syringe may be used in any application where it is desirable to provide for the direct administration of medical fluids from a vented syringe while permitting the plunger delivery of medical fluids as needed.

The disclosed vented syringe overcomes several challenges discovered with respect to certain conventional syringes. One challenge with certain conventional syringes is that medical fluids cannot be administered via IV delivery with certain conventional syringes without intermediate steps or components. Because the use of additional steps and/or components adds complexity, the use of conventional syringes with IV delivery is undesirable.

Therefore, in accordance with the present disclosure, it is advantageous to provide a vented syringe as described herein that eliminates or substantially reduces intermediate steps or components needed for administration of medical fluids. The disclosed vented syringe provides an air intake channel that permits direct IV administration of medical fluids from the vented syringe while still permitting plunger delivery of medical fluids.

An example of a vented syringe that permits direct IV administration of medical fluids is now described.

Figure 1:
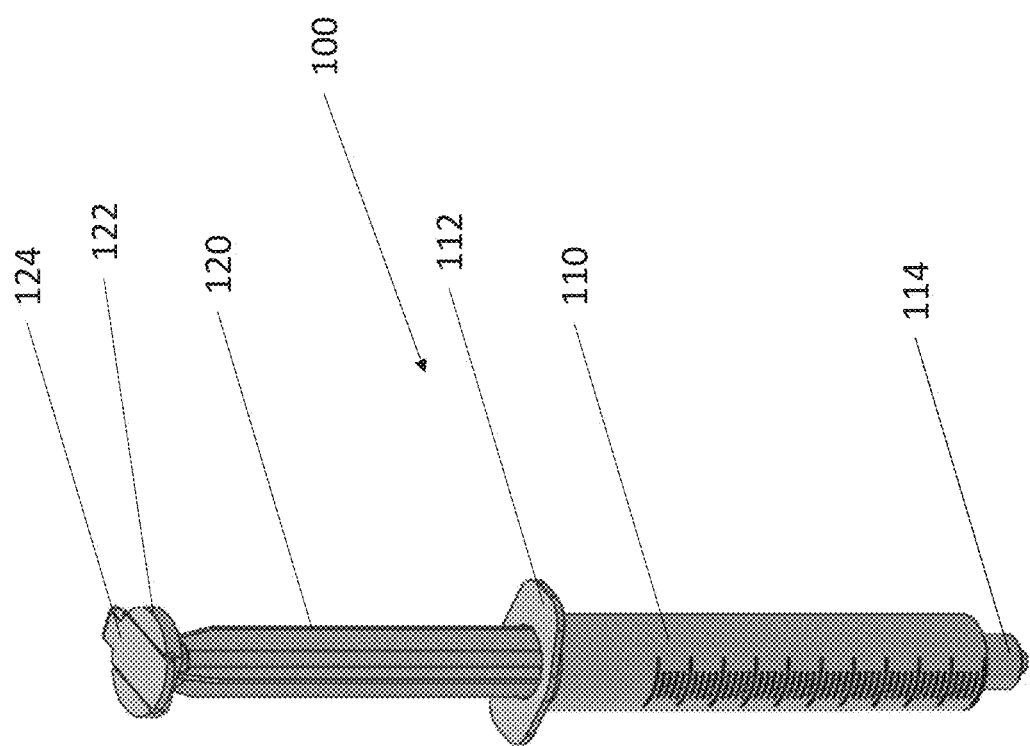
FIG. 1 is a perspective view of a syringe, in accordance with various aspects of the present disclosure.

FIG. 1 is a perspective view of a syringe 100, in accordance with various aspects of the present disclosure. In the depicted example, the vented syringe 100 can dispense medical fluids by either actuating the plunger body 120 relative to the syringe body 110 or by functioning as an IV drip.

As illustrated, the plunger body 120 is slidable relative to the syringe body 110. In some embodiments, the syringe body 110 can be keyed to the features of the plunger body 120 to prevent or limit rotational movement of the plunger body 120 relative to the syringe body 110. In some embodiments, the plunger body 120 can be retracted relative to the syringe body 110 to draw in a medical fluid via the aperture or connector 114. Optionally, the connector 114 can be any suitable medical connector including a Luer connector. In some embodiments, a pressure differential or vacuum within the syringe body 110 relative to the atmosphere maintains drawn medical fluid within the vented syringe 100.

In some applications, to expel or otherwise dispense the medical fluid within the syringe 100, the plunger body 120 can be depressed relative to the syringe body 110. The plunger body 120 can slide or otherwise travel within the syringe body 110 to administer the medical fluid via the connector 114.

In some embodiments, the plunger body 120 includes a thumb pad 122 at an end of the plunger body 120 to allow for ergonomic operation of the vented syringe 100. Further, the syringe body 110 can include syringe body extensions 112 to allow the clinician to move the plunger body 120 relative to the syringe body 110 both during a drawing motion of the plunger body 120 and the contraction motion of the plunger body 120.

In some applications, after a medical fluid is drawn into the vented syringe 100, the vented syringe 100 can be configured to dispense the medical fluid as an IV drip or otherwise dispense the medical fluid without actuating the plunger body 120 relative to the syringe body 110.

In the depicted example, a cap 124 disposed at the end of the plunger body 120 can be removed to expose the medical fluid within the syringe body 110 to atmospheric pressure. By exposing the medical fluid within the syringe body 110 to atmospheric pressure, any pressure differential or vacuum within the syringe body 110 relative to the atmosphere can be equalized or overcome, permitting an IV drip or flow of medical fluid through the connector 114.

Advantageously, by operating the vented syringe 100 with cap 124 in a closed position, the vented syringe 100 can be utilized to administer medical fluids by actuating the plunger body 120 relative to the syringe body 110. Further, by removing the cap 124 from the plunger body 120, the vented syringe 100 can be utilized to administer medical fluids via an IV drip. In some embodiments, the cap 124 is disposed within or forms a portion of the thumb pad 122. Optionally, the cap 124 can be press fit into the plunger body 120.

Figure 2:
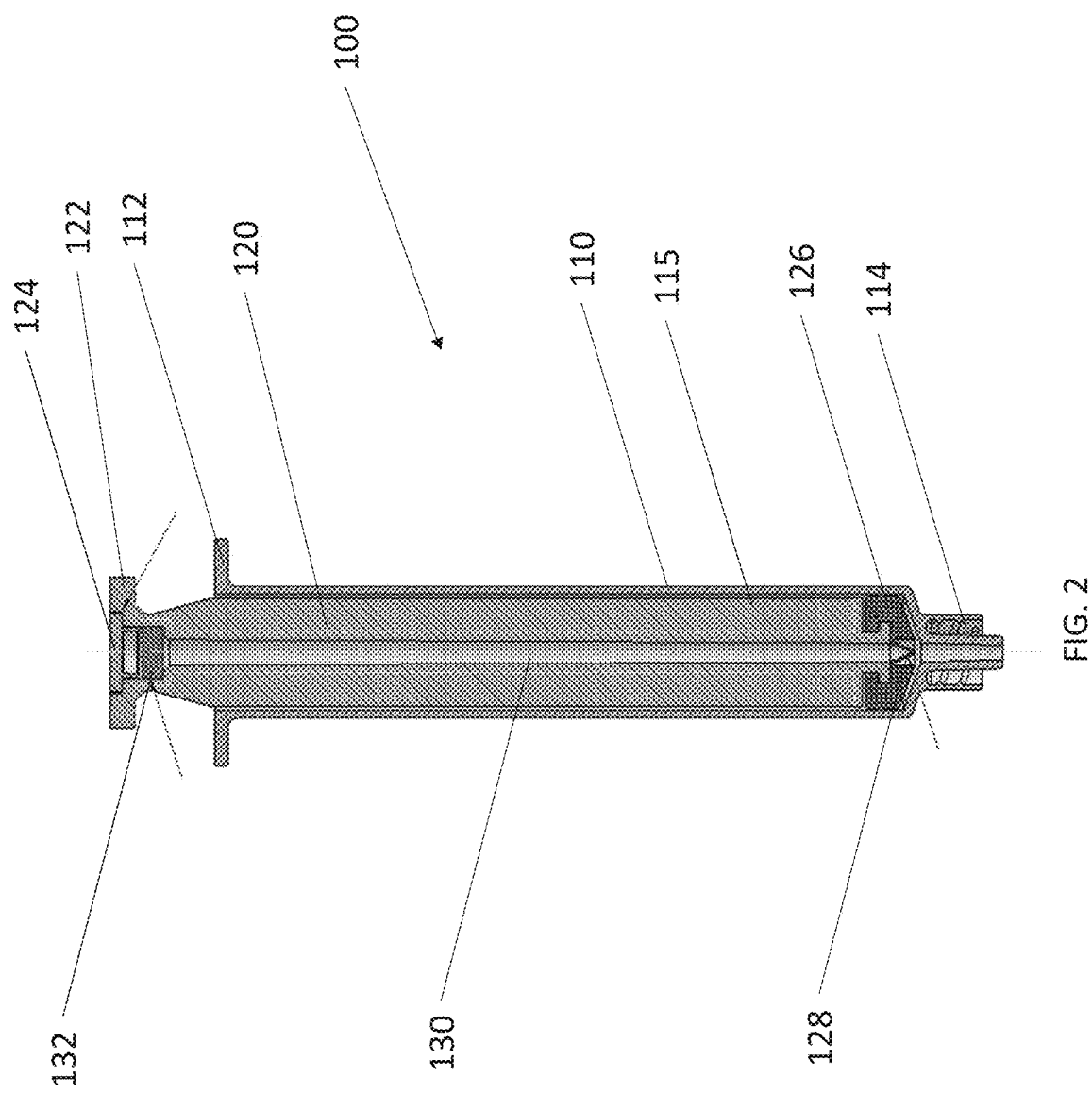
FIG. 2 is a cross-sectional view of the syringe of FIG. 1, in accordance with various aspects of the present disclosure.
Figure 3:
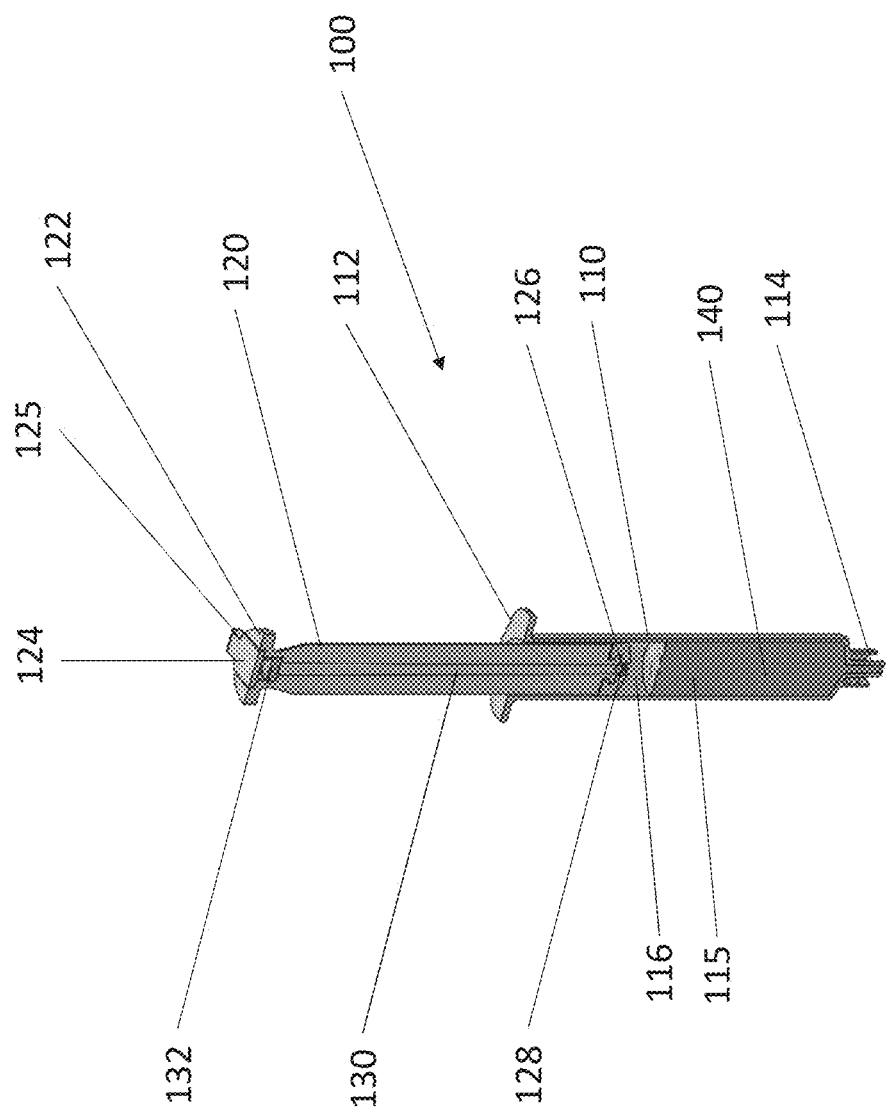
FIG. 3 is a cross-sectional view of a syringe in a drawing configuration, in accordance with various aspects of the present disclosure.

FIG. 2 is a cross-sectional view of the syringe 100 of FIG. 1, in accordance with various aspects of the present disclosure. As illustrated, FIG. 2 illustrates the vented syringe 100 in an assembled position. FIG. 3 is a cross-sectional view of a syringe 100 in a drawing configuration, in accordance with various aspects of the present disclosure. With reference to FIGS. 2 and 3, the vented syringe 100 can be utilized to draw medical fluid 140 into the syringe cavity 115 within the syringe body 110.

In some applications, to draw fluid into the vented syringe 100, the plunger body 120 is retracted relative to the syringe body 110. By retracting the plunger body 120, the plunger seal 126 coupled at an end of the plunger body 120 moves within the syringe cavity 115 of the syringe body 110 to expand a syringe volume 116. In some embodiments, the plunger seal 126 is in sealing engagement with the inner walls of the syringe cavity 115 to cooperatively define the syringe volume 116 within the syringe cavity 115. The plunger seal 126 can be an expandable and/or elastomeric seal. During the drawing process, by retracting the plunger body 120 and the plunger seal 126, the syringe volume 116 expands.

As the syringe volume 116 expands, the syringe volume 116 experiences a negative pressure differential or a vacuum therein. Due to the pressure differential in the syringe volume 116 compared to the connector 114, medical fluid 140 from the connector 114 is drawn into the syringe volume 116. Medical fluid 140 can be drawn in via the connector from a vial or any other suitable container. In some applications, the vented syringe 100 can be prefilled with medical fluid 140.

During the fluid drawing process, a one-way valve 128 can prevent medical fluid 140 from entering the air intake channel 130 and contacting the filter 132. As illustrated, the air intake channel 130 extends from one end of the plunger body 120, adjacent to the plunger seal 126 to an opposite end of the plunger body 120, adjacent to the thumb pad 122.

While the air intake channel 130 can facilitate air flow or pressure equalization to the syringe volume 116 when IV drip functionality is desired, fluid flow of medical fluid 140 into the air intake channel 130 may not be desired. In some applications, it is desired to prevent or stop medical fluid 140 from entering the air intake channel 130 to prevent contamination or clogging of the filter 132, contamination of the medical fluid 140, and/or to prevent the migration of medical fluid 140 out of the vented syringe 100.

In the depicted example, the one-way valve 128 can prevent medical fluid 140 from being drawn from the syringe volume 116 to the air intake channel 130. During operation, the one-way valve 128 can close or collapse to prevent flow into the air intake channel 130 as the plunger seal 126 is retracted within the syringe body 110. In some embodiments, the one-way valve 128 can be a duckbill valve that prevents backflow from the syringe volume 116 into the air intake channel 130. Optionally, the one-way valve 128 can be integrally formed with the plunger seal 126.

After the drawing process, the pressure differential from the syringe volume 116 to the connector 114 allows the medical fluid 140 to remain in the syringe volume 116. As illustrated, the cap 124 can prevent airflow from entering the air intake channel 130 and equalizing the pressure differential in the syringe volume 116 until desired.

Figure 4:
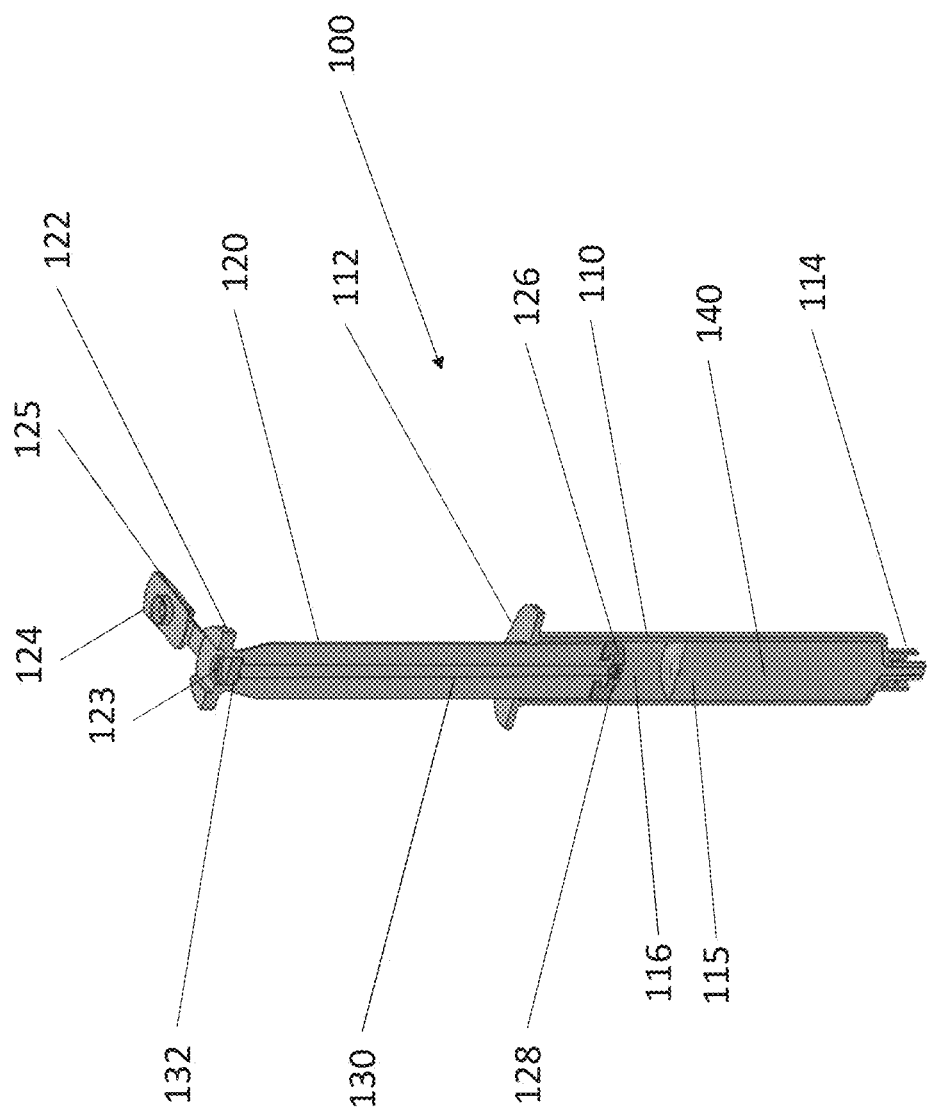
FIG. 4 is a cross-sectional view of a syringe in a venting configuration, in accordance with various aspects of the present disclosure.
Figure 5:
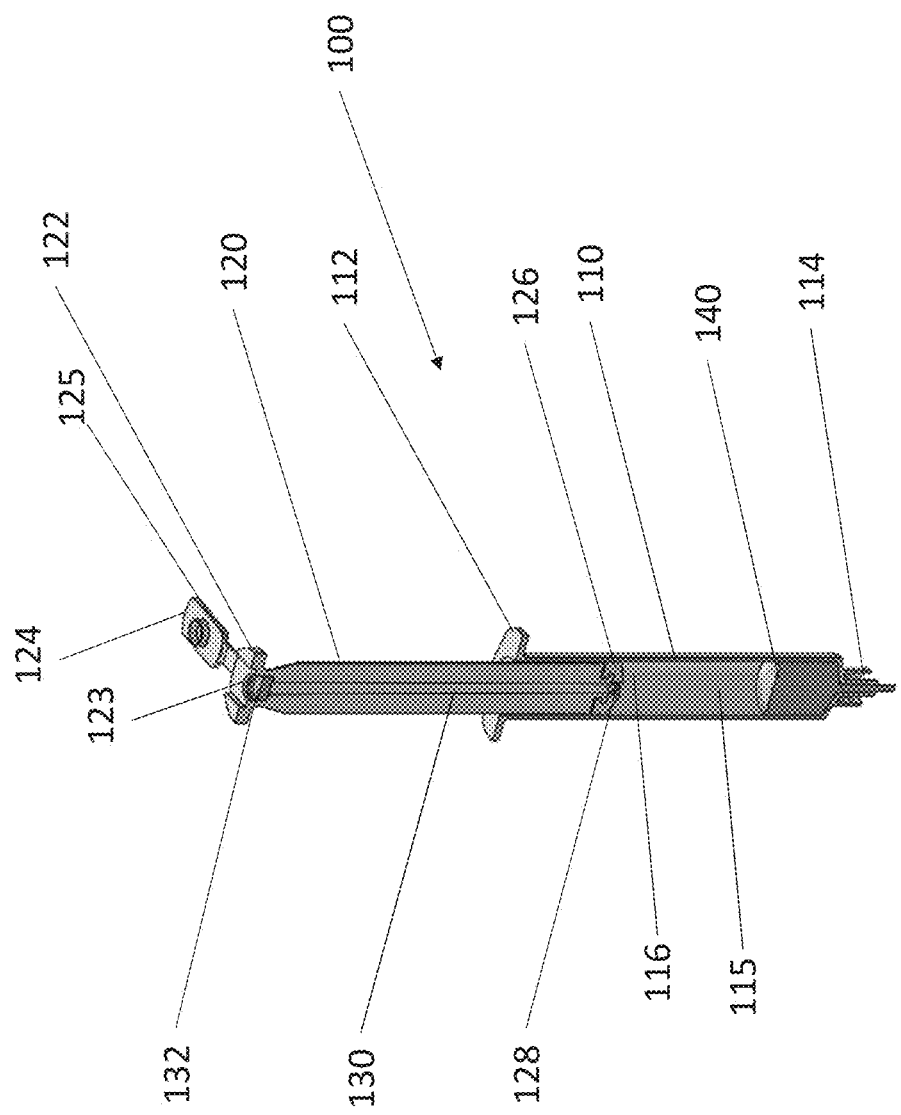
FIG. 5 is a cross-sectional view of the syringe of FIG. 4 in the venting configuration, in accordance with various aspects of the present disclosure.
Figure 6:
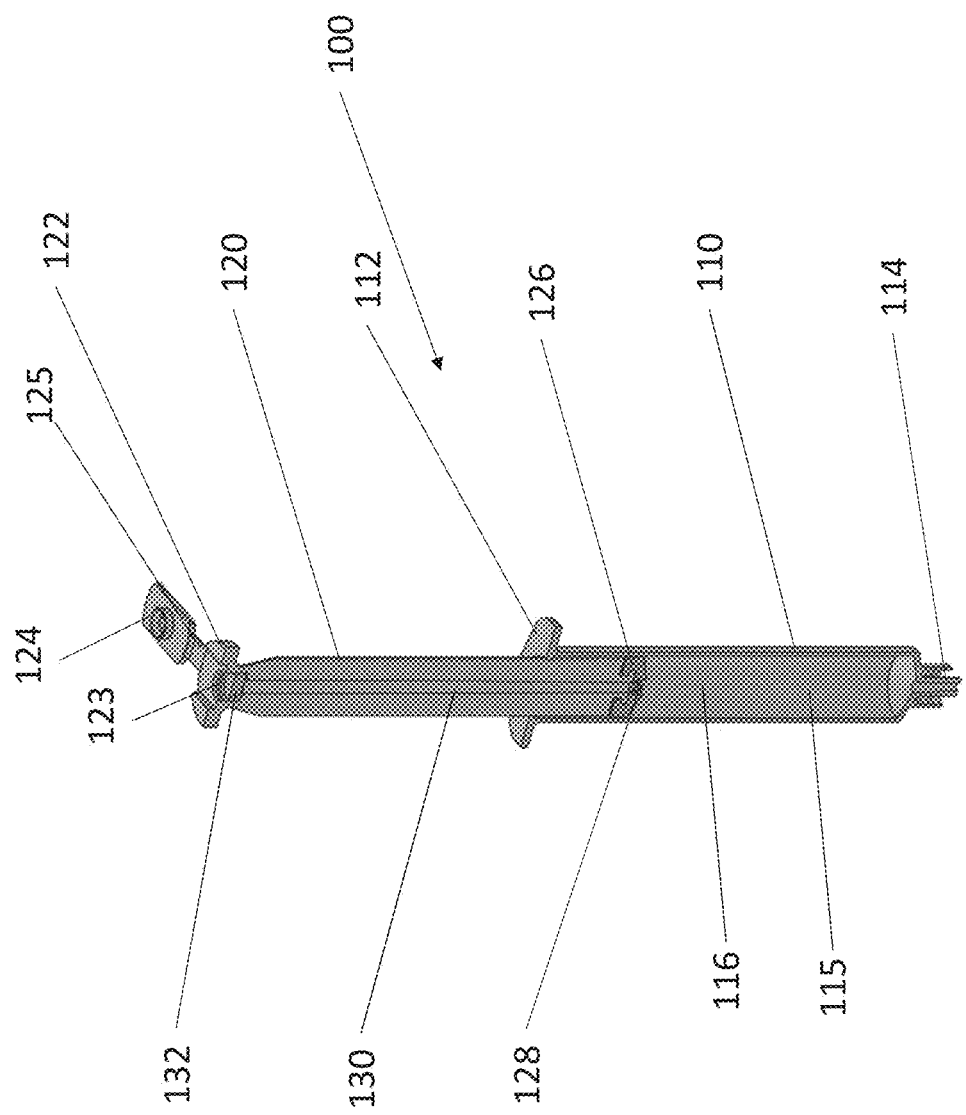
FIG. 6 is a cross-sectional view of the syringe of FIG. 4 in the venting configuration, in accordance with various aspects of the present disclosure.

FIGS. 4-6 are cross-sectional views of a syringe 100 in a venting configuration, in accordance with various aspects of the present disclosure. As illustrated in FIGS. 4-6, the vented syringe 100 can permit the IV administration of the medical fluid retained or stored in the syringe volume 116.

During operation, the cap 124 is removed from an end of the air intake channel 130 to allow air flow and/or atmospheric pressure to be received by the air intake channel 130. As shown, the cap 124 can be removed from the thumb pad 122 of the plunger body 120. The cap 124 can be releasably engaged with a receptacle 123 formed in the thumb pad 122. Optionally, the cap 124 can be retained by a tether 125 when the cap 124 is disengaged from the air intake channel 130.

Upon removal of the cap 124, the air intake channel 130 can permit fluid communication between the atmosphere surrounding the vented syringe 100 and the syringe volume 116 containing the medical fluid 140. Atmospheric pressure introduced via the air intake channel 130 can equalize the pressure or otherwise release the vacuum within the syringe volume 116, permitting the medical fluid 140 to exit or drip through the connector 114. In some embodiments, the vented syringe 100 can be coupled to an infusion pump or positioned above a patient to allow flow to the patient. As shown in FIG. 6, flow can continue until all of the medical fluid 140 is administered.

In some embodiments, the air intake channel 130 is integrally formed with the plunger body 120. Optionally, the air intake channel 130 can be formed separately from the plunger body 120. The air intake channel 130 can have a generally circular cross-sectional profile. Optionally, the air intake channel 130 can have a cross-sectional profile that varies.

In some embodiments, air flow introduced to the syringe volume 116 can pass through the one-way valve 128. The one-way valve 128 can be configured to allow airflow from the atmosphere, through the air intake channel 130 and into the syringe volume 116. In some embodiments, the one-way valve 128 is a duckbill valve that can allow flow through the flattened portion of the valve.

In some embodiments, the air intake channel 130 can include a filter 132 to filter the air flow passing through the air intake channel 130. The filter 132 can be any suitable filter that allows air flow therethrough while preventing contaminants from entering the medical fluid 140.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A vented syringe, comprising:
   a syringe body defining a syringe cavity;
   a plunger body disposed at least partially within the syringe cavity, wherein the plunger body extends continuously between a first end and a second end, the plunger body comprising:
   an air intake channel defined within the plunger body and extending continuously between the first end and the second end of the continuous plunger body; and
   a thumb pad disposed at the first end of the plunger body;
   a filter disposed inwardly adjacent to the thumb pad at the first end of the plunger body and in fluid communication with the air intake channel;
   a plunger seal disposed at the second end of the plunger body and sealingly engaged with the syringe cavity, wherein the plunger body is stationary relative to the plunger seal; and
   a one-way valve disposed at the second end of the plunger body, wherein the one-way valve, the plunger seal, and the syringe cavity cooperatively define a syringe volume within the syringe cavity, the one-way valve is in fluid communication with the air intake channel and the syringe volume, and the one-way valve is configured to prevent fluid flow from the syringe volume to the air intake channel and permit fluid flow from the air intake channel to the syringe volume.

2. The vented syringe of claim 1, wherein the syringe body further comprises an aperture in fluid communication with the syringe volume.

3. The vented syringe of claim 1, wherein the plunger body is slidable relative to the syringe body.

4. The vented syringe of claim 1, wherein the plunger body further comprises a cap removably engaged with the air intake channel at the first end of the plunger body.

5. The vented syringe of claim 4, wherein the cap is configured to prevent fluid flow to the air intake channel when engaged with the air intake channel.

6. The vented syringe of claim 4, wherein the plunger body further comprises a cap receptacle to releasably engage the cap.

7. The vented syringe of claim 4, wherein the filter is positioned between the cap and the second end of the plunger body.

8. The vented syringe of claim 1, wherein the one-way valve is configured to collapse to prevent fluid flow from the syringe volume to the air intake channel.

9. The vented syringe of claim 1, wherein the one-way valve comprises a duckbill valve.

10. The vented syringe of claim 1, wherein the one-way valve is integrally formed with the plunger seal.

11. The vented syringe of claim 1, wherein the plunger seal is disposed around a portion of the second end of the plunger body.

12. The vented syringe of claim 1, wherein the plunger seal is disposed around a portion of the air intake channel.

13. The vented syringe of claim 1, wherein the one-way valve is configured to prevent liquid within the air intake channel and permit air flow from the air intake channel to the syringe volume.

14. A vented syringe, comprising:
   a syringe body defining a syringe cavity;
   a plunger body disposed at least partially within the syringe cavity, wherein the plunger body extends continuously between a first end and a second end, the plunger body comprising:
   an air intake channel defined within the plunger body and extending continuously between the first end and the second end of the continuous plunger body; and
   a thumb pad disposed at the first end of the plunger body;
   a filter disposed inwardly adjacent to the thumb pad at the first end of the plunger body and in fluid communication with the air intake channel;
   a plunger seal disposed at the second end of the plunger body and sealingly engaged with the syringe cavity, wherein the plunger body is stationary relative to the plunger seal; and
   a one-way valve disposed at the second end of the plunger body, wherein the one-way valve, the plunger seal, and the syringe cavity cooperatively define a syringe volume within the syringe cavity and expansion of the syringe volume provides a vacuum within the syringe volume, the one-way valve is in fluid communication with the air intake channel and the syringe volume, wherein the one-way valve is configured to prevent fluid flow into the air intake channel during expansion of the syringe volume and permit fluid flow from the air intake channel to the syringe volume to release the vacuum within the syringe volume.

15. The vented syringe of claim 14, wherein the plunger body is slidable relative to the syringe body.

16. The vented syringe of claim 14, wherein the plunger body further comprises a cap removably engaged with the air intake channel at the first end of the plunger body.

17. The vented syringe of claim 16, wherein the cap is configured to prevent fluid flow to the air intake channel when engaged with the air intake channel.

18. The vented syringe of claim 14, wherein the plunger seal is disposed around a portion of the second end of the plunger body.

19. The vented syringe of claim 14, wherein the plunger seal is disposed around a portion of the air intake channel.

20. A vented syringe, comprising:
   a syringe body defining a syringe cavity;
   a plunger body disposed at least partially within the syringe cavity, the plunger body comprising:
   an air intake channel defined within the plunger body and extending between a first end and a second end of the plunger body; and
   a thumb pad disposed at the first end of the plunger body;
   a filter disposed inwardly adjacent to the thumb pad at the first end of the plunger body and in fluid communication with the air intake channel;

a plunger seal disposed at the second end of the plunger body and sealingly engaged with the syringe cavity, wherein the plunger body is stationary relative to the plunger seal; and a one-way valve disposed at the second end of the plunger body, wherein the one-way valve, the plunger seal, and the syringe cavity cooperatively define a syringe volume within the syringe cavity, the one-way valve is in fluid communication with the air intake channel and the syringe volume, and the one-way valve is configured to prevent fluid flow from the syringe volume to the air intake channel and permit fluid flow from the air intake channel to the syringe volume, and to prevent liquid within the air intake channel and permit air flow from the air intake channel to the syringe volume.

* * * * *